(12) United States Patent
Studer

(10) Patent No.: US 10,941,319 B2
(45) Date of Patent: Mar. 9, 2021

(54) PRINTING AN ADHESIVE PATTERN ON AN ANTI-FOULING SUPPORT

(71) Applicants: ALVEOLE, Paris (FR); CENTRE NATIONAL DE LA RECHERCHE SCIENTIFIQUE—CNRS, Paris (FR); UNIVERSITÉ DE BORDEAUX, Bordeaux (FR)

(72) Inventor: Vincent Studer, Bordeaux (FR)

(73) Assignees: ALVEOLE, Paris (FR); CENTRE NATIONAL DE LA RECHERCHE SCIENTIFIQUE—CNRS, Paris (FR); UNIVERSITÉ DE BORDEAUX, Bordeaux (FR)

(*) Notice: Subject to any disclaimer, the term of this patent is extended or adjusted under 35 U.S.C. 154(b) by 0 days.

(21) Appl. No.: 15/515,210

(22) PCT Filed: Oct. 2, 2015

(86) PCT No.: PCT/EP2015/072874
§ 371 (c)(1),
(2) Date: Mar. 29, 2017

(87) PCT Pub. No.: WO2016/050980
PCT Pub. Date: Apr. 7, 2016

(65) Prior Publication Data
US 2017/0218230 A1    Aug. 3, 2017

(30) Foreign Application Priority Data
Oct. 3, 2014  (FR) .................................. 1459497

(51) Int. Cl.
C09J 5/02       (2006.01)
B01J 19/00      (2006.01)
(Continued)

(52) U.S. Cl.
CPC ................ C09J 5/02 (2013.01); B01J 19/00 (2013.01); B05D 1/18 (2013.01); B05D 3/065 (2013.01);
(Continued)

(58) Field of Classification Search
CPC ......... C09J 5/02; C09J 2205/006; B01J 19/08
See application file for complete search history.

(56) References Cited

U.S. PATENT DOCUMENTS 5,677,196 A * 10/1997 Herron ................. C08G 65/329
                                                    436/518
7,147,687 B2 * 12/2006 Mirkin ............... A61K 49/0067
                                                     75/343
(Continued)

FOREIGN PATENT DOCUMENTS

WO    2006/084482 A1    8/2006
WO    2013/135844 A1    9/2013

OTHER PUBLICATIONS

International Search Report issued in PCT/EP2015/072874 dated Feb. 5, 2016 (6 pages).
(Continued)

*Primary Examiner* — Dah-Wei D. Yuan
*Assistant Examiner* — Kristen A Dagenais-Englehart
(74) *Attorney, Agent, or Firm* — Osha Bergman Watanabe & Burton LLP

(57) ABSTRACT

Process for printing an adhesive pattern on a polymer brush extending at the surface of a support (1), forming a nanometric anti-fouling layer (2), the process comprising the following steps: —placing the layer (2) in contact with a first aqueous solution (4) containing a benzophenone, —then illuminating the layer with radiation (3) at a wavelength within the absorption spectrum of benzophenone, according to the pattern and according to a surface energy.

16 Claims, 1 Drawing Sheet

(51) Int. Cl.
*C40B 50/18* (2006.01)
*B05D 3/06* (2006.01)
*B05D 5/10* (2006.01)
*B05D 1/18* (2006.01)
*B82Y 40/00* (2011.01)
*B01J 19/08* (2006.01)
*G01N 33/543* (2006.01)

(52) U.S. Cl.
CPC ............... *B05D 3/067* (2013.01); *B05D 5/10* (2013.01); *C40B 50/18* (2013.01); *B01J 19/08* (2013.01); *B01J 2219/00596* (2013.01); *B01J 2219/00711* (2013.01); *B82Y 40/00* (2013.01); *C09J 2301/416* (2020.08); *C09J 2471/006* (2013.01); *C09J 2483/006* (2013.01); *G01N 33/54353* (2013.01)

(56) References Cited

U.S. PATENT DOCUMENTS

| | | | |
|---|---|---|---|
| 2008/0139689 A1* | 6/2008 | Huang | C08F 291/00 522/67 |
| 2008/0206752 A1* | 8/2008 | Balakirev | C08J 7/18 435/6.11 |
| 2014/0202632 A1* | 7/2014 | Wang | B05D 7/16 156/345.3 |
| 2015/0147485 A1* | 5/2015 | Studer | C40B 60/14 427/553 |

OTHER PUBLICATIONS

Written Opinion of the International Searching Authority issued in PCT/EP2015/072874 dated Feb. 5, 2015 (6 pages).
Cosnier, Serge; et al.; "An electrogenerated poly(pyrrole-benzophenone) film for the photografting of proteins," Chemical Communications, Jan. 23, 2003; pp. 414-415 (2 pages).
Leckband, D.; et. al.; "Grafted poly(ethylene oxide) brushes as nonfouling surface coatings;" Journal of Biomaterials Science, Polymer Edition; Apr. 2, 2012, pp. 1125-1147 (25 pages).
Office Action issued in the counterpart Chinese Patent Application No. 201580053960.7, dated Aug. 13, 2019 (11 pages).

* cited by examiner

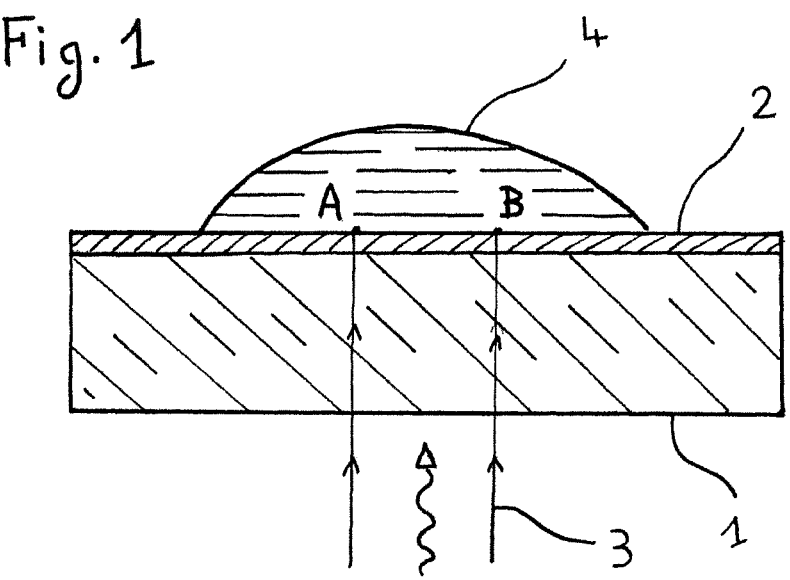
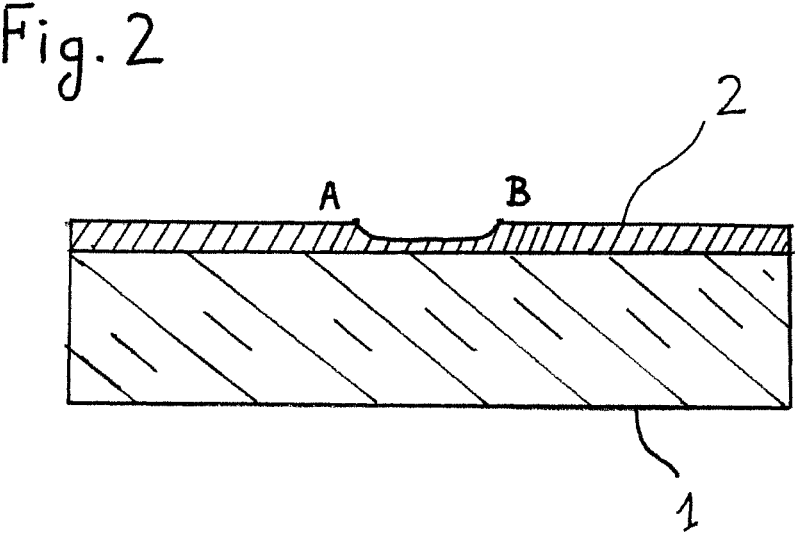

PRINTING AN ADHESIVE PATTERN ON AN ANTI-FOULING SUPPORT

TECHNICAL FIELD

The present invention relates to the field of grafting a protein onto a substrate, according to an optically defined pattern.

BACKGROUND

The publication of international application number WO 2013/135844 (hereinafter "STUDER" or "the publication") discloses a device for the microstructured grafting of proteins onto a substrate, or photochemical printing device. In the publication, a mixture, in aqueous solution, of a benzophenone (BP) and of a protein is illuminated in places according to a pattern on top of a substrate and a durable transfer of the protein at the illuminated places is obtained, producing the printing. However, the process described in the publication transfers the protein onto the substrate, in the presence of BP and at the same time as the illumination.

This device involves a combination, at the same location, of a lighting device for illuminating according to an image of a pattern on the substrate and a microfluidic device that makes it possible to convey an aqueous solution simultaneously containing a protein and a BP. This results in a problem of bulkiness of the printing system and also a risk of damaging the protein by the combined action of the benzophenone and the light from the lighting device. Ideally, it would be useful to print a pattern that is only adhesive for the protein, without adhered protein, onto a substrate, by means of the lighting system. An actual pattern would subsequently develop on the substrate, in contact with an aqueous solution of a protein, for example a fluorescent protein, the protein attaching preferentially to the illuminated parts in the adhesive pattern to form the actual pattern. Such a solution is nevertheless governed, for a protein, by the availability of a process capable of producing a latent or subsequently developed adhesive pattern, which is printed onto a support covered by a protein anti-fouling layer. A protein anti-fouling layer is understood to mean a layer made from a material that has no attachment of proteins to said layer, on the timescale of carrying out the printing that it is proposed to produce.

Such a substrate covered by its anti-fouling layer, or anti-fouling substrate, may be formed in particular by a support such as a hard support, one example of which is a glass of optical quality which is transparent for the light from the lighting system, or such as a soft support, one example of which is a PDMS, the glass or the PDMS being covered by a polymer brush material, or polymer attaching as a brush to the support by chains of molecules, such as PEG and polyNipam. The polymer chains are, for anti-fouling substrates of this type, attached at one of their ends to the support and free at the other end, like the bristles of a brush.

Other techniques such as photolithography applied to a protein anti-fouling substrate through a mask using laser ablation of patterns of anti-fouling materials on an anti-fouling substrate make it possible in the prior art to obtain anti-fouling supports having patterns that allow the subsequent selective grafting of a protein to the substrate, according to the illuminated zones of the substrate from which the polymer brush or anti-fouling material has been removed, by light energy.

It is considered that ablation of material is caused by the illumination of the substrate and that the differences in level produced make possible a pseudoscopic image of the subsequent actual image. When these differences are observed by the optical phase-contrast technique which is only sensitive to the optical path, the adhesive pattern may be attributed in an equivalent manner to an ablation of anti-fouling material or to a change in the nature of the material modifying its optical index and providing a subsequent preferential adhesion of proteins to the zones of polymer chains that have been illuminated. Other techniques that enable the latent image to be observed (in particular atomic-force microscopy, ellipsometry, x-ray analysis, etc.) make it possible in certain cases to prove that the latent image is due to a complete ablation of the PEG layer for these techniques. Such ablation techniques do not therefore make it possible to produce concentration gradients, the ablation of the PEG or anti-fouling layer being a priori complete.

It would finally be desirable to have available a process for producing an anti-fouling or polymer brush support having adhesion that is proportional or continuously variable with the exposure of the brush to an illumination, according to a pattern, without molecules necessarily being adhered to the brush at the same time as the illumination. It would instead be desirable for these molecules to be adhered to the brush in a deferred manner.

GENERAL PRESENTATION

The following definitions apply to the present application:

"Adhesive pattern": denotes a surface pattern according to which certain molecules, in particular proteins (and especially antibodies), nanoshells, DNA (deoxyribonucleic acid) strands or RNA strands or bacteria are distributed in a time-stable manner on a support covered by an anti-adhesive or anti-fouling or polymer brush layer, outside of said adhesive pattern. Since the pattern is defined outside of an anti-adhesive or anti-fouling zone or a set of anti-adhesive or anti-fouling zones, an adhesive pattern may also be defined on a substrate as a set of zones or patterns that are more adhesive for the molecules of interest than the supplementary surface of the set of zones on the substrate. A difference in adhesion effect, necessary for the existence of a pattern, may be predicted for a polymer brush, without coming into contact with an aqueous solution of a molecule, by at least two techniques that are available in the prior art:
  Atomic-force microscopy, which makes it possible to demonstrate a reduction in the length of the polymer chains of the brush, such a reduction then causing a reduction in the anti-adhesive effect or an increase in the adhesion effect in these zones.
  Phase-contrast microscopy, which makes it possible to demonstrate a variation in the optical path through the brush in the most adhesive zones, such a variation then being associated with an adhesion effect variation.

"Polymer brush": denotes a nanometric layer (i.e. the thickness of which is on the nanometer scale, namely typically between 1 nm and 100 nm) which is anti-fouling, in particular for proteins, nanoshells, DNA strands and bacteria, such a nanometric layer being present at the surface of a support in order to form an anti-fouling substrate. It is estimated, at the date of the present application, that such a brush consists of a set of polymer chains grafted to the surface of a support, this set extending in a zone having a thickness of between 1 nm and 20 nm at the surface of the support for PEG and between 1 nm and 30 nm for polyNI-PAM. It is estimated that between 1 nm and 20 nm, such a brush has anti-adhesion or anti-fouling properties, in particular for proteins, nanoshells, DNA strands or bacteria. A polyethylene glycol or "PEG" layer or a poly(N-isopropylacrylamide) or polyNIPAM layer are examples of polymer brushes.

"Thickness" denotes, for a polymer brush, the measure of the distance to the support from the free ends of the polymer chains forming the brush. For example, for PEG, the thickness of the layer is controlled by the length of the PEG chains, that is to say the number of ethylene glycol monomers making up these chains. These chains may in particular be inclined with respect to the substrate or compressed or modified in any manner similar to an action on the bristles of a brush in order to print a relief or a thickness variation on the free surface of the brush.

Within this context, the invention relates to a process for printing an adhesive pattern on a polymer brush extending at the surface of a support forming a nanometric anti-fouling layer, the process comprising the following steps:
  placing the layer in contact with a first aqueous solution containing a benzophenone,
  then illuminating the layer with radiation at a wavelength within the absorption spectrum of the benzophenone, according to the pattern and according to a surface energy.
In variants of the process:
  the thickness of the layer is between 1 nm and 20 nm;
  the wavelength is chosen between 300 nm and 400 nm;
  the polymer is a polyethylene glycol (PEG);
  the polymer is a polyNIPAM;
  the support is a glass;
  the support is a PolyDiMethylSiloxane (PDMS);
  the surface energy of the illumination transmitted to the PEG layer is between 10 mJ/mm$^2$ and 1000 mJ/mm$^2$;
  the surface energy of the illumination transmitted to the polyNIPAM layer is between 100 mJ/mm$^2$ and 10000 mJ/mm$^2$;
  the Young's modulus of the PDMS support is less than 15 kPa.

The invention also relates to a process as above, for printing a pattern of a protein on the polymer brush, comprising the following additional steps:
  rinsing to eliminate the contact between the layer and the first solution,
  then placing the layer in contact with a second aqueous solution containing the protein.

The invention also relates to a process as above, for printing a pattern of nanoshells on the polymer brush, comprising the following additional steps:
  rinsing to eliminate the contact between the layer and the first solution,
  placing the layer in contact with a second solution containing the nanoshells.

The invention also relates to a process as above, for printing a pattern of DNA strands on the polymer brush, comprising the following additional steps:
  rinsing to eliminate the contact between the layer and the first solution,
  placing the layer in contact with a second solution containing the DNA strands.

The invention also relates to an application of the process for printing an adhesive pattern, to the production of an adhesive pattern having an adhesion gradient at the surface of the support, by spatial variation of the surface energy.

BRIEF DESCRIPTION OF THE DRAWINGS

The invention will be better understood in connection with the list of figures below, wherein:

FIG. 1 represents, in cross section, an anti-fouling substrate composed of a glass support and a layer of material that is anti-fouling, in particular for proteins, nanoshells or DNA strands, that is to say a polymer brush grafted or attached to the support. The substrate is covered with a drop of an aqueous solution containing benzophenone over all or some of the polymer brush. A zone AB of the layer, covered with benzophenone, is illuminated through the support (through the drop would also be practicable) via radiation comprising wavelengths within the absorption spectrum of benzophenone, i.e. radiation between 300 nm and 400 nm.

FIG. 2 represents the substrate rinsed of the drop from FIG. 1 and having a latent image represented in a illustrated manner by a hollow in the surface of the anti-fouling material at the zone AB. Such a material is capable of being used to print in particular a pattern of a protein, of nanoshells or of DNA or RNA strands according to a pattern corresponding to the surface of the zone AB. Specifically, the illumination of the polymer brush in the presence of benzophenone potentially renders the polymer brush adhesive in the zone AB and enables the subsequent adhesion in particular of a protein, of nanoshells or of DNA strands, by subsequently placing the polymer brush layer in contact, respectively, with in particular a solution of the protein, a solution of nanoshells or of DNA strands. An illumination according to a set of zones like AB thus enables the production of an adhesive pattern or an adhesive pattern of molecules on a polymer brush, for molecules for which the brush is normally non-adhesive.

DETAILED DESCRIPTION OF EXAMPLE(S)

In a first embodiment, disclosed with reference to FIG. 1 for the reference numbers between parentheses, are an anti-fouling substrate composed of a glass support (1) and a layer (2) of a polymer brush material which is, in this first embodiment, PEG or polyNIPAM.

In this first embodiment, radiation (3) illuminates the layer (2) over a zone AB (AB), here through a support (1) chosen to be transparent for the radiation used, a drop (4) of an aqueous benzophenone solution is deposited on the layer (2) covering the zone AB (AB). In an equivalent manner, it would be possible to illuminate the layer through the drop (4), over the same zone AB.

The radiation used comprises at least one wavelength within the absorption spectrum of benzophenone, which spectrum usefully extends in practice between 300 nm and 400 nm. Preferentially, within this range use will be made of radiation having a wavelength of less than 390 nm, in this case the exposure time of the layer to the radiation will be minimized.

The lower the absorption of benzophenone at the chosen wavelength, the greater the power of the light source will have to be or the longer the exposure time of the illuminated zone will have to be, the dose of the radiation received, equal to the product of the lighting power and the exposure time to the light, being the parameter governing the obtaining of the effect of the invention.

Since no protein to be grafted is in solution, the radiation will if necessary be of higher power than a power that gives rise to the destruction of a protein to be subsequently grafted and will only be limited by the surface density of light energy accepted by the layer, without degradation. However, the presence of benzophenone makes it possible, for PEG, to use optical powers 10 to 100 times lower than for ablation or masking techniques.

An energy density between 10 mJ/mm$^2$ and 1000 mJ/mm$^2$ can thus be used to obtain the appearance of an adhesive pattern on PEG. The invention may thus be satisfied with a source that produces an illumination of 2 mW over a square having sides of 400 microns for a wavelength of an ultraviolet line at 372 nm from a semiconductor laser. For polyNipam on a PDMS support, a usable energy density is between 100 mJ/mm$^2$ and 10000 mJ/mm$^2$. The same semiconductor laser source may again be used by simply multiplying the exposure times for PEG by 10.

In a first step of the process of this embodiment, the anti-fouling substrate is placed in contact with a drop of aqueous benzophenone solution, then in a second step a zone AB of the anti-fouling layer of the substrate is illuminated with the ultraviolet light source.

Any optical system enabling the energy of the source to be focused on the zone AB or on a set of zones at the same time can be used and such systems are known from the prior art. A microscope with a micromirror array can thus be envisaged for producing the lighting system for this embodiment. Similarly, the drop may be replaced by a film of aqueous benzophenone solution, brought into contact with the layer, then rinsed after illumination by known microfluidic means.

FIG. 2 represents the polymer brush formed as a nanometric layer, thus rinsed of the drop of the benzophenone solution and provided, in an illustrated manner, with a hollow latent pattern that is itself also nanometric with regard to its depth, in the zone AB. In order to be developed, this hollow or latent pattern needs to be subsequently brought into contact with molecules or molecular assemblies capable of adhering to the support at this hollow in a polymer brush (proteins, nanoshells, DNA strands, bacteria, etc.), the adhesion of these molecules according to the latent pattern then takes place in the presence of these molecules in aqueous solution, at the zones of the layer which have been illuminated (here AB) in the presence of benzophenone. The adhesion of molecules takes place without provision of light energy. The molecules are simply adsorbed on the polymer brush at the latent pattern or adhesive pattern. An actual pattern of molecules is thus formed on the brush. In particular if the molecules are fluorescent, it is possible to then make an image thereof by techniques known in the prior art in order to demonstrate the result of the adhesion.

However, even without bringing into contact with an aqueous solution, for example a solution of proteins, it is possible to predict, after insolation of the brush, whether the effect of the invention will be obtained, independently of the production of a subsequent actual pattern, by measuring, after illumination, whether there are hollows of nanometric depth in the brush at the illuminated locations using an atomic-force microscope (AFM), or by observing whether there are optical path variations in the brush, optically, by phase-contrast microscopy at these same locations. It is thus possible to select, without other experimentation, the polymer brushes suitable for the process of the invention, in particular as being those for which a reduction in the length of the polymer chains of the brush is observed after illumination in the presence of benzophenone.

In a second embodiment of the invention, the device from FIG. 2 is brought into contact with an aqueous solution of a protein or an aqueous solution of nanoshells. The choice of the nature of the proteins or of the nanoshells is made from the proteins and nanoshells capable of adhering to the support in order to obtain the most durable possible actual image.

It is thus possible, with the process of this second embodiment, to obtain an actual image of the zone AB for example by using a fluorescent protein, but more generally a pattern of a protein on the protein anti-fouling substrate that was used. Furthermore, the properties, under illumination, of the anti-fouling substrates make it possible to produce a fluorescence having a value that varies continuously with the illumination or the dose of optical radiation received by the zone AB and more generally a concentration of proteins, of nanoshells or of DNA strands that varies continuously with the illumination in this zone, even if this zone corresponds to the resolution limit of the optical lighting system, without recourse to densities of binary points to simulate variable concentrations of proteins.

It is thus possible to apply the invention to the production of adhesion gradients in a concentration direction for example of a protein, of nanoshells or of DNA strands, along the surface of the substrate or of the anti-fouling layer, by aligning several zones of type AB end-to-end and by varying the surface energy delivered to these zones, for example by illuminating them with variable surface zones (in J/m$^2$), during the step of illuminating the polymer brush in the presence of benzophenone or of printing the latent image or adhesive pattern.

For example, a continuously variable adhesive effect for proteins has been obtained by variable dose illumination in the presence of benzophenone on a PEG brush, for a thickness reduction of between 0 nm reduction (no adhesion or outside-pattern zone) and 2 nm reduction (maximum adhesion) for PEG polymer brushes having a thickness estimated at 5 nm outside of the adhesion zones.

In the embodiments presented, a concentration range in millimoles of benzophenone per liter of aqueous solution (mmol/l) from 5 mmol/l to 50 mmol/l was used.

The invention is industrially applicable within the field of substrate production for printing adhesive patterns of a protein on a polymer brush.

The invention claimed is:

1. A process for printing an adhesive pattern on a polymer brush extending at the surface of a support forming a nanometric anti-fouling layer, the process comprising the following steps:
    placing the layer in contact with a first aqueous solution containing a benzophenone,
    then illuminating the layer with a radiation at a wavelength within the absorption spectrum of the benzophenone, according to the pattern and according to a surface energy, thereby creating an adhesive pattern which is a zone or a set of zones on the polymer brush that are more adhesive for molecules of interest than the supplementary surface of the zone or set of zones on the polymer brush, the adhesive pattern being a hollow latent pattern on the polymer brush and not being covered by the molecules of interest but left bare.

2. The process as claimed in claim 1, wherein the thickness of the layer is between 1 nm and 20 nm.

3. The process as claimed in claim 2, wherein the wavelength is chosen between 300 nm and 400 nm.

4. The process as claimed in claim 3, wherein said polymer is a polyethylene glycol (PEG).

5. The process as claimed in claim 3, wherein said polymer is a poly(N-isopropylacrylamide).

6. The process as claimed in claim 3, wherein said support is a glass.

7. The process as claimed in claim 3, wherein said support is a polydimethylsiloxane (PDMS).

8. The process as claimed in claim 4, wherein the surface energy of the illumination transmitted to the PEG layer is between 10 mJ/mm$^2$ and 1000 mJ/mm$^2$.

9. The process as claimed in claim 5, wherein the surface energy of the illumination transmitted to the poly(N-isopropylacrylamide) layer is between 100 mJ/mm$^2$ and 10 000 mJ/mm$^2$.

10. The process as claimed in claim 7, wherein the Young's modulus of the PDMS is less than 15 kPa.

11. The process as claimed in claim 1, for printing a pattern of molecules or molecular assemblies of interest on the polymer brush, comprising the following additional steps:
rinsing to eliminate the contact between the layer and the first solution,
then placing the layer in contact with a second aqueous solution containing the molecules or molecular assemblies of interest.

12. The process as claimed in claim 11, for printing a pattern of nanoshells on the polymer brush, wherein the molecules or molecular assemblies of interest are nanoshells.

13. The process as claimed in claim 11, for printing a pattern of DNA strands on the polymer brush, wherein the molecules or molecular assemblies of interest are DNA strands.

14. The process as claimed in claim 11, wherein an adhesive pattern having an adhesion gradient at the surface of the support, is produced by spatial variation of the surface energy.

15. The process as claimed in claim 11, for printing a pattern of proteins on the polymer brush, wherein the molecules or molecular assemblies of interest are proteins.

16. The process as claimed in claim 11, wherein, when the layer is brought into contact with the molecules or molecular assemblies of interest, the molecules or molecular assemblies of interest are adsorbed on the adhesive pattern, the adsorption taking place without provision of light energy.

* * * * *